United States Patent
Chen et al.

(12) 
(10) Patent No.: US 6,255,085 B1
(45) Date of Patent: Jul. 3, 2001

(54) PRODUCTION OF CHITOSAN AND CHITIN

(75) Inventors: Mei-Huei Chen, Hsinchu; Hing-Yuen Chan, Miaoli; Chih-Lu Wu; Su-Hui Chuang, both of Hsinchu; Ing-Er Hwang, Kaohsiung; Yen-Lin Chen, Taoyuan; Gwo-Fang Yuan, Hsinchu, all of (TW)

(73) Assignee: Food Industry Research & Development Institute (TW)

( * ) Notice: Subject to any disclaimer, the term of this patent is extended or adjusted under 35 U.S.C. 154(b) by 0 days.

(21) Appl. No.: 09/349,807

(22) Filed: Jul. 8, 1999

(51) Int. Cl.$^7$ ............... C12P 19/26; C12P 19/04; C12N 1/14; A01N 43/04

(52) U.S. Cl. .............. 435/101; 435/254.1; 435/911; 435/84; 514/55; 536/20

(58) Field of Search ................. 435/101, 254.1, 435/84, 911; 514/55; 536/20

(56) References Cited

U.S. PATENT DOCUMENTS

| | | | |
|---|---|---|---|
| 5,232,842 | | 8/1993 | Park et al. ........................... 435/101 |
| 5,429,942 | * | 7/1995 | Kock et al. ........................... 435/134 |
| 5,905,035 | * | 5/1999 | Okada et al. ........................... 435/101 |

FOREIGN PATENT DOCUMENTS

| | | |
|---|---|---|
| 0 531 991 A2 | 3/1993 | (EP) . |
| 8-013250 | 1/1996 | (JP) . |

OTHER PUBLICATIONS

Jong et al Computer Biosis Abstract 1985:422674 Mycotaxon (1985) 23 (0) 261–264.*

Hsiu et al Computer Caplus Abstract 1995:44987 Zhong Nongye Huaxue Huizhi (1994) 32(3) 276–283.*

Mei et al Computer Caplus Abstract 1995:931006Zhong Nongye Huazue Huizhi (1995) 33(4) 404–411.*

Mei et al Computer Caplus Abstract 1996:242307 J.Sci Food Agric (1996) 70(4) 509–514, 1985.*

Fortin, Caroline et al., "Elucidation of the Mechanism Involved in the Regulation of Protease Production By Immobilized *Myxococcus xanthus* Cells," Biotechnology Letters, vol. 12, No. 12, pp. 913–918, 1990.

Kubo, Takamasa et al., "Effects of the Cultivation pH on the Degree of Deacetylation of Chitosan Produced by Rhizopus . . . ," Nippon Nōgeikagaku Kaishi, vol. 66, No. 11, pp. 1641–1643, 1992, English Abstract only.

McGahren, W.J. et al., "Chitosan by Fermentation," Process Biochemistry, vol. 19, pp. 88–90, 1984.

Rane, Kishore D. et al., Production of Chitosan by Fungi, Food Biotechnology, vol. 7, No. 1, pp. 11–33, 1993.

Shimahara, Kenzo et al., "Screening of Mucoraceae Strains Suitable for Chitosan Production," Elsevier, London, pp. 171–178, 1989.

Yokoi, Haruhiko et al., "Chitosan Production from Shochu Distillery Wastewater by Funguses," Journal of Fermentation and Bioengineering, vol. 85, No. 2, pp. 246–249, 1998.

Zetelaki–Horvath, K. et al., "Kinetic Analysis of Protein Synthesis in Fungi," Acta Alimentaria, vol. 4, No.2, pp. 181–188, 1975.

Zetelaki–Horvath, K. et al., "Kinetic Analysis of Protein Synthesis in Fungi," Acta Alimentaria, vol. 5, No. 2, pp. 169–178, 1976.

Tan et al., "The chitosan yield . . . ," Carbohydraft Polymers, 30:239–242, 1996.

* cited by examiner

*Primary Examiner*—Herbert J. Lilling
(74) *Attorney, Agent, or Firm*—Fish & Richardson P.C

(57) ABSTRACT

The invention relates to a method of producing chitin or chitosan by culturing a *Rhizopus azygosporus* fungus or an *Actinomucor taiwanensis* fungus and isolating chitosan or chitin from the culture.

12 Claims, No Drawings

PRODUCTION OF CHITOSAN AND CHITIN

BACKGROUND OF THE INVENTION

Chitin is a highly insoluble N-acetylated polymer of β-(1,4)-D-glucosamine. Chitosan is an acid-soluble deacetylated form of chitin. Chitin, chitosan, and derivatives thereof are used in a number of industrial applications, including the production of viscosity control agents, adhesives, chromatography carriers, paper-strengthening agents, flocculent agents, food additives, drugs, and cosmetics.

Chitin can be manufactured by the deproteination and decalcification of crab or shrimp shells. Chitosan can then be obtained by deacetylating chitin with a hot alkali solution. This chitosan production process has a number of unfavorable characteristics. For example, the process requires expensive heat energy and caustic alkali, which is a potential health hazard. The process also produces large amounts of waste, thereby necessitating significant disposal costs. In addition, the supply of shrimp or crab shells is highly dependent upon seasonal and environmental factors, leading to unpredictable limitations on production capacity.

SUMMARY OF THE INVENTION

The invention is based on the discovery that unexpectedly high yields of chitosan and chitin can be produced from the fungus *Actinomucor taiwanensis* and from the fungus *Rhizopus azygosporus*.

Accordingly, the invention features a method of producing chitosan or chitin by (1) culturing a *Rhizopus azygosporus* fungus or an *Actinomucor taiwanensis* fungus in a medium to form a culture, and (2) isolating chitosan or chitin from the cells. For example, chitosan and chitin can be isolated from the culture by separating the fungal cells from the culture and isolating the chitosan or chitin from the separated cells.

The invention also includes a method of producing chitosan or chitin by (1) culturing a fungus of the family Mucoraceae in a medium useful in the methods of the invention to form a culture, and (2) isolating chitosan or chitin from the fungal culture.

A medium useful for the methods of the invention can include about 5 to 60 g/L (e.g., about 30 g/L) corn steep liquor, about 10–100 g/L (e.g., about 50 g/L) glucose, about 0.01 to 30 g/L (e.g., about 2.5 g/L) ammonium sulfate, or other suitable ingredients.

The methods of the invention allow surprisingly high-yield production of chitosan or chitin from a culture containing a *Rhizopus azygosporus* or *Actinomucor taiwanensis* fungus. Further, it has been discovered that a medium containing corn steep liquor, glucose, yeast extract, and ammonium sulfate is capable of increasing the output of chitin and chitosan from a fungal culture. The methods of the invention, therefore, provide an alternative to producing chitin and chitosan without reliance on environmentally harmful chemicals or the variable abundance of the crustacean crop.

Other features or advantages of the present invention will be apparent from the following detailed description, and also from the claims.

DETAILED DESCRIPTION

The invention relates to high yield production of chitosan or chitin from fungal cultures belonging to the family Mucoraceae.

Particular fungi useful in the methods of the invention include *Rhizopus azygosporus* and *Actinomucor taiwanensis*. Both of these organisms are available upon request from the Culture Collection and Research Center (CCRC), Food Industry and Research Development Institute, No. 331, Shih-Ping Road, Hsinchu 300, Taiwan, Republic of China. *R. azygosporus* is available as Catalog No. CCRC31558, and *A. taiwanensis* is available as Catalog No. CCRC31559.

Procedures for culturing fungi are well known in the art. For example, YM agar can be inoculated with a fungus, and the inoculated agar incubated at 25° C. to 37° C. for 3 to 6 days. Spores obtained from the fungus are suspended in liquid to achieve a $10^4$ to $10^7$ cfu/ml stock. This stock is directly inoculated into a fermentation medium.

The fermentation medium can have an initial pH ranging from 3 to 8 and can contain 10 to 100 g/L of a carbon source (e.g., glucose, sucrose, corn starch, molasses, or soybean oil), 5 to 60 g/L of a nitrogen source (e.g., soybean meal, peptone, or corn steep liquor), 0.5 to 20 g/L of yeast extract, 0.01 to 30 g/L $(NH_4)_2SO_4$, 0 to 3 g/L $K_2HPO_4$, 0 to 3 g/L NaCl, 0 to 15 g/L $MgSO_4.7H_2O$, and/or 0 to 0.3 g/L $CaCl_2$. The fungus is grown in the fermentation medium for an additional two to four days.

Chitosan can be isolated and purified from fungal mycelia by standard methods. For example, alkaline and acid treatment can be used to isolate chitosan as described in McGahren et al., Process Biochem 19:88–90, 1984. Additional details and procedures for isolating chitosan can be found in European Application No. 0531991 A2; Yokoi et al., J Fermen Bioeng 85:246–249, 1998; U.S. Pat. No. 5,232,842,; Rane et al., Food Biotech 7:11–33, 1993; and Hang, Biotech Lett 12:911–912, 1990.

In general, the cell mass is separated from the fermentation broth and washed with distilled water. The cells are then treated with 0.5 to 2 N NaOH, and the alkaline mixture incubated at 121° C. for 15 minutes. The solid material is then pelleted by centrifugation and washed with distilled water and ethanol. The washed material is treated with a 2% acetic acid solution and incubated at 95° C. for 12 hours. The resulting slurry is then isolated by centrifugation, yielding an acid-soluble supernatant (containing chitosan) and an acid-insoluble precipitate (containing chitin).

The pH of the supernatant is adjusted to 10 with 2 N NaOH, thereby precipitating out the chitosan. The chitosan is finally washed with distilled water and freeze-dried. The acid-insoluble precipitate is also washed with distilled water and freeze-dried. This acid-insoluble and alkali-insoluble fraction is purified chitin.

Without further elaboration, it is believed that one skilled in the art can, based on the above disclosure and the description below, utilize the present invention to its fullest extent. The following examples are to be construed as merely illustrative of how one skilled in the art can practice the invention and are not limitative of the remainder of the disclosure in any way. Any publications cited in this disclosure are hereby incorporated by reference.

The results for the following examples are summarized in Table 2, which appears after the Examples.

EXAMPLE 1

Spore suspension of *Rhizopus azygosporus* from 4-day slant cultures was inoculated directly into 250 ml shaker flasks containing 100 ml of fresh fermentation medium. Fermentation was carried out at 28° C. for 48 hours, while shaking at 200 rpm. Each liter of medium contained 10 g of a nitrogen source (soybean meal, peptone, or corn steep liquor), 20 g of a carbon source (glucose or corn starch), 1 g yeast extract, 5 g $(NH_4)_2SO_4$, 1 g $K_2HPO_4$, 1 g NaCl, 5 g $MgSO_4.7H_2O$, and 0.1 g $CaCl_2$.

The cell mass was recovered from the fermented broth and treated with 1 N NaOH at 121° C. for 15 minutes. The alkali-insoluble material was suspended in 2% acetic acid, and the mixture incubated at 95° C. for 12 hours to solubilize the chitosan. Chitosan was precipitated by adjusting pH of the acid-soluble supernatant to 10. The chitosan was then washed, dried, and weighed. The acid-insoluble material, chitin, also was washed, dried, and weighed. Yields were calculated in terms of grams chitin or chitosan per liter of culture, and the results are presented in Table 2. The highest yields of chitin and chitosan were achieved using the medium containing corn starch and peptone.

EXAMPLE 2

A spore suspension of *Actinomucor taiwanensis* from 4-day slant cultures was inoculated directly into 250 ml shaker flasks containing 100 ml of fermentation medium. Fermentation and chitosan and chitin isolation was performed as described in Example 1, and the results presented in Table 2. High yields of chitin and chitosan could be achieved using the medium containing corn steep liquor and glucose.

EXAMPLE 3

*R. azygosporus* was cultured and processed as described in Example 1 above, except that all media contained peptone as the nitrogen source, and the source of carbon was varied among glucose, corn starch, sucrose, molasses, and soybean oil. Inclusion of corn starch led to a high yield of 0.9 g/L for both chitosan and chitin, while inclusion of soybean oil led to the highest yield of 1.5 g/L for chitin for this Example (Table 2).

EXAMPLE 4

*A. taiwanensis* was cultured and processed as described in Example 2 above, except that all media contained corn steep liquor as the nitrogen source, and the source of carbon was varied among glucose, corn starch, sucrose, molasses, and soybean oil. Inclusion of glucose as the carbon source led to the best yield of both chitin and chitosan for this Example (Table 2).

EXAMPLE 5

*R. azygosporus* was cultured and processed as described in Example 1, except that each liter of medium contained 30 g corn steep liquor, 50 g glucose, 2 g yeast extract, 2.5 g $(NH_4)_2SO_4$, and 0.05 g $CaCl_2$. This culture led to a high yield of 1.1 g/L for chitosan (Table 2).

EXAMPLE 6

*A. taiwanensis* was cultured and processed as described in Example 2, except that each liter of medium contained 30 g corn steep liquor, 50 g glucose, 2 g yeast extract, 2.5 g $(NH_4)_2SO_4$, and 0.05 g $CaCl_2$. This culture led to the highest combined yield of chitosan (1.7 g/L) and chitin (1.1 g/L) (Table 2).

EXAMPLE 7

*A. taiwanensis* was cultured and processed as described in Example 6, except that the medium contained 0.5 g $K_2HPO_4$ per liter instead of $CaCl_2$. This culture led to a high yield of 1.4 g/L for chitosan.

TABLE 2

| EXAMPLE/ strain | Nitrogen Source | | | Carbon Source | | | | | Salt | | | | | Yield (g/L) | |
| --- | --- | --- | --- | --- | --- | --- | --- | --- | --- | --- | --- | --- | --- | --- | --- |
| | S.M. | peptone | C.S.L. | glucose | C.S. | sucrose | molasses | S.O. | $(NH4)_2SO_4$ | $K_2HPO_4$ | NaCl | $MgSO_4$ | $CaCl_2$ | chitosan | chitin |
| 1/R.a. | X | | | X | | | | | X | X | X | X | X | 0.3 | 0.9 |
| | | X | | X | | | | | X | X | X | X | X | 0.7 | 0.6 |
| | | | X | X | | | | | X | X | X | X | X | 0.5 | 0.7 |
| | X | | | | X | | | | X | X | X | X | X | 0.2 | 0.7 |
| | | X | | | X | | | | X | X | X | X | X | 0.9 | 0.9 |
| | | | X | | X | | | | X | X | X | X | X | 0.4 | 0.8 |
| 2/A.t. | X | | | X | | | | | X | X | X | X | X | 0.5 | 0.4 |
| | | X | | X | | | | | X | X | X | X | X | 0.7 | 0.6 |
| | | | X | X | | | | | X | X | X | X | X | 0.9 | 0.9 |
| | X | | | | X | | | | X | X | X | X | X | 0.5 | 0.8 |
| | | X | | | X | | | | X | X | X | X | X | 0.6 | 1.0 |
| | | | X | | X | | | | X | X | X | X | X | 0.6 | 0.6 |
| 3/R.a. | | X | | X | | | | | X | X | X | X | X | 0.7 | 0.6 |
| | | X | | | X | | | | X | X | X | X | X | 0.9 | 0.9 |
| | | X | | | | X | | | X | X | X | X | X | 0.4 | 0.7 |
| | | X | | | | | X | | X | X | X | X | X | 0.8 | 0.6 |
| | | X | | | | | | X | X | X | X | X | X | 0.5 | 1.5 |
| 4/A.t. | | | X | X | | | | | X | X | X | X | X | 0.9 | 0.9 |
| | | | X | | X | | | | X | X | X | X | X | 0.6 | 0.6 |
| | | | X | | | X | | | X | X | X | X | X | 0.6 | 0.4 |
| | | | X | | | | X | | X | X | X | X | X | 0.3 | 0.3 |
| | | | X | | | | | X | X | X | X | X | X | 0.2 | 0.7 |
| 5/R.a. | | | X | X | | | | | X | | | | X | 1.1 | 0.6 |
| 6/A.t. | | | X | X | | | | | X | | | | X | 1.7 | 1.1 |
| 7/A.t. | | | X | X | | | | | X | X | | | | 1.4 | 0.7 |

The abbreviations used in Table 2 are as follows: "R.a." stands for *Rhizopus azygosporus*; "A.t." stands for *Actinomucor taiwanensis*; "S.M." stands for soybean meal;

"C.S.L." stands for corn steep liquor; "C.S." stands for corn starch; and "S.O." stands for soybean oil. All cultures described in Table 2 contained yeast extract.

The results in Examples 1–7 above indicated that (1) *A. taiwanensis* and *R. azygosporus* are superior producers of chitin and chitosan, and (2) media containing corn steep liquor, glucose, and ammonium sulfate can increase the yield of chitin and chitosan produced by fungi.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A method of producing chitosan or chitin, the method comprising culturing an *Actinomucor taiwanensis* fungus in a medium to form a culture, and isolating chitosan or chitin from the culture, wherein the medium comprises about 5 to 60 g/L corn steep liquor.

2. The method of claim 1, wherein the medium comprises about 30 g/L corn steep liquor.

3. The method of claim 1, wherein the medium further comprises 0.01 to 30 g/L ammonium sulfate.

4. The method of claim 3, wherein the medium comprises about 2.5 g/L ammonium sulfate.

5. The method of claim 1, wherein the medium further comprises about 10–100 g/L glucose.

6. The method of claim 5, wherein the medium comprises about 50 g/L glucose.

7. The method of claim 1, further comprising separating fungal cells from the culture, and wherein the chitosan or chitin is isolated from the separated fungal cells.

8. A method of producing chitosan or chitin, the method comprising culturing an *Actinomucor taiwanensis* fungus in a medium to form a culture, and isolating chitosan or chitin from the culture, wherein the medium comprises about 10–100 g/L glucose.

9. The method of claim 8, wherein the medium comprises about 50 g/L glucose.

10. The method of claim 8, wherein the medium further comprises about 0.01 to 30 g/L ainmoniun sulfate.

11. The method of claim 10, wherein the medium further comprises about 2.5 g/L ammonium sulfate.

12. The method of claim 8, further comprising separating fungal cells from the culture, and wherein the chitosan or chitin is isolated from the separated fungal cells.

* * * * *